United States Patent
Maxfield et al.

(10) Patent No.: US 11,110,230 B2
(45) Date of Patent: Sep. 7, 2021

(54) NEEDLE SHIELD REMOVER

(71) Applicant: SHL MEDICAL AG, Zug (CH)

(72) Inventors: Brian Maxfield, Delray Beach, FL (US); Jason Frost, Boca Raton, FL (US); Dane Kris, Deerfield Beach, FL (US)

(73) Assignee: SHL MEDICAL AG, Zug (CH)

( * ) Notice: Subject to any disclaimer, the term of this patent is extended or adjusted under 35 U.S.C. 154(b) by 118 days.

(21) Appl. No.: 16/607,285

(22) PCT Filed: Apr. 23, 2018

(86) PCT No.: PCT/EP2018/060337
§ 371 (c)(1),
(2) Date: Oct. 22, 2019

(87) PCT Pub. No.: WO2018/202458
PCT Pub. Date: Nov. 8, 2018

(65) Prior Publication Data
US 2020/0046910 A1 Feb. 13, 2020

Related U.S. Application Data

(60) Provisional application No. 62/492,599, filed on May 1, 2017.

(51) Int. Cl.
*A61M 5/32* (2006.01)

(52) U.S. Cl.
CPC .................... *A61M 5/3204* (2013.01)

(58) Field of Classification Search
CPC ............ A61M 5/3204; A61M 5/3202; F04C 2270/0421
See application file for complete search history.

(56) References Cited

U.S. PATENT DOCUMENTS

| 4,636,201 A | 1/1987 | Ambrose et al. |
| 2015/0065961 A1* | 3/2015 | Daniel ............... A61M 5/321 604/198 |

FOREIGN PATENT DOCUMENTS

| CN | 101939036 A | 1/2011 |
| CN | 105709312 A | 6/2016 |

(Continued)

OTHER PUBLICATIONS

Oxford English Dictionary Online, "Adjacent" Definition, https://www.oed.com/oed2/00002709;jsessionid=97CEEF537A9A926F58AF9CBBD01C388F (Year: 1989).*

(Continued)

*Primary Examiner* — Bhisma Mehta
*Assistant Examiner* — Rachel T. Smith
(74) *Attorney, Agent, or Firm* — McDonnell Boehnen Hulbert & Berghoff LLP

(57) ABSTRACT

A needle shield remover is presented having a generally tubular body with a longitudinal extension and a number of grip elements arranged at a distal area of the body, where the grip elements extend radially inwards from a circumference of the body. At least one longitudinally extending cut-out in the body and adjacent to the grip elements engage an outer surface of a needle shield when the needle shield remover is pushed onto the needle shield, where the at least one cut-out enables a generally radial outwardly bias of the grip elements during the pushing action to facilitate mounting of the needle shield remover on the needle shield.

18 Claims, 3 Drawing Sheets

(56) References Cited

FOREIGN PATENT DOCUMENTS

| WO | 03/051423 A2 | 6/2003 |
| WO | 2009/087355 A1 | 7/2009 |
| WO | 2012/103140 A1 | 8/2012 |
| WO | WO-2012103140 A1 * | 8/2012 | .............. A61M 5/32 |
| WO | 2018/069031 A1 | 4/2018 |

OTHER PUBLICATIONS

Chinese Office Action for CN Application No. 201880025965.2, dated Feb. 26, 2021.
International Search Report and Written Opinion for Int. App. No. PCT/EP2018/060337, dated Aug. 6, 2018.

* cited by examiner

NEEDLE SHIELD REMOVER

CROSS REFERENCE TO RELATED APPLICATIONS

The present application is a U.S. National Phase application pursuant to 35 U.S.C. § 371 of International Application No. PCT/EP2018/060337 filed Apr. 23, 2018, which claims priority to U.S. Provisional Patent Application No. 62/492,599 filed May 1, 2017. The entire disclosure contents of these applications are herewith incorporated by reference into the present application.

TECHNICAL AREA

The present disclosure relates to a needle shield remover.

BACKGROUND

A large number of medicament delivery devices that are designed for self-medication are arranged with prefilled syringes or the like medicament containers that in turn are provided with medicament delivery members such as injection needles. In order to keep the injection needles sterile, a needle shield is often attached to and surrounds the needle. One very common type of needle shield is a so called flexible needle shield or FNS. The FNS is often made of a resilient material such as rubber, having an inner cavity in which the needle is placed. The dimensions of the cavity are chosen such that a tight fit is obtained around the needle, thereby preventing any contamination of the sterile needle.

However, the tight fit means that there is a friction fit, thus requiring some force in order to pull the needle shield off the needle. Many medicament delivery devices are therefore provided with needle shield removers, which in turn often are attached to safety caps at a proximal end of the medicament delivery device. The safety cap is in that regard arranged with a grip part so that the user may be provided with a good grip for the pulling action.

The needle shield removers may have different designs. Often they have a generally tubular body with a diameter that is somewhat larger than the diameter of the needle shield so that the body may fit around the needle shield coaxially. Different types of grip elements on the body have been developed for providing a proper grip of the surface of the needle shield so that it may be removed when pulling the safety cap, against the friction force. Different types of grip elements have entailed tongues, protrusions and other types of contact elements that engage with the outer surface of the needle shield. Many of these solutions display drawbacks such as varying grip capabilities due to tolerance differences between engaging components, difficulties in obtaining a good grip on the rubber material of the FNS, complicated manufacturing and/or assembly, just to mention a few drawbacks. Similar problems occur with rigid needle shields, RNS, wherein an inner needle shield of a flexible material is provided with an outer housing or shell of a more rigid material. The challenges of gripping such an RNS are more or less the same as for FNS even though the material properties of the outer surfaces are different. There is thus room for improvement of needle shield removers for removing needle shields.

SUMMARY

In the present application, when the term "distal part/end" is used, this refers to the part/end of the device, or the parts/ends of the members thereof, which during use of the device is located the furthest away from the medicament delivery site of the patient. Correspondingly, when the term "proximal part/end" is used, this refers to the part/end of the device, or the parts/ends of the members thereof, which during use of the device is located closest to the medicament delivery site of the patient.

The aim of the disclosed needle shield remover is to remedy the drawbacks of the state of the art removers. This aim is solved by a needle shield remover with the features according to the independent patent claims. Preferable embodiments of the needle shield remover form the subject of the dependent patent claim.

According to one feature of the disclosed needle shield remover, it comprises a generally tubular body having a longitudinal extension. Preferably the body is arranged with a number of grip elements arranged at a distal area of the body, wherein the grip elements may extend radially inwards from a circumference of the body. The number of grip elements may for example vary depending on the desired function and on the diameter of the body.

Further, at least one longitudinally extending cut-out may be arranged at the distal area of the body adjacent the grip elements, wherein the grip elements may be designed to engage an outer surface of a needle shield when the needle shield remover is pushed onto the needle shield, and the at least one cut-out may enable a generally radial outwardly bias of the grip elements during the pushing action, facilitating mounting of the needle shield remover on the needle shield.

According to another aspect, the tubular body may have such an extension in the longitudinal direction in relation to a length of the needle shield that the grip elements are placed after a distal end wall of said needle shield when mounted. Thus the at least one grip element is returned to its original unbiased position, wherein the at least one grip element may be in contact with a distally directed end surface of the needle shield.

According to one favourable solution, the grip elements may comprise a number of discrete tongues. Further, the tongues may have an inclination in relation to the longitudinal direction in the proximal direction of the body. The tongues may in that respect have a certain flexing resiliency in the generally radial direction, allowing a biasing movement of the tongues also when the needle shield remover is pushed onto the needle shield.

Further, a number of longitudinally extending cut-outs may be arranged between adjacent tongues, adding to the flexing properties of the tongues.

In order to further enhance the flexing and biasing properties of the distal end of the body, the at least one cut-out may be provided with a section having a larger width, creating a band-shaped section at the distal end of the body.

The size of the section having a larger width may be that it constitutes generally half of the circumference of the body. Moreover, a proximal area of the wider section is arranged with inclined surfaces.

Preferably the body may be arranged with attachment elements for a grip part of a protective cap.

These and other aspects of, and advantages with, the present disclosure will become apparent from the following detailed description of the disclosure and from the accompanying drawings.

BRIEF DESCRIPTION OF DRAWINGS

In the following detailed description of the disclosure, reference will be made to the accompanying drawings, of which

DETAILED DESCRIPTION

Figure 1:
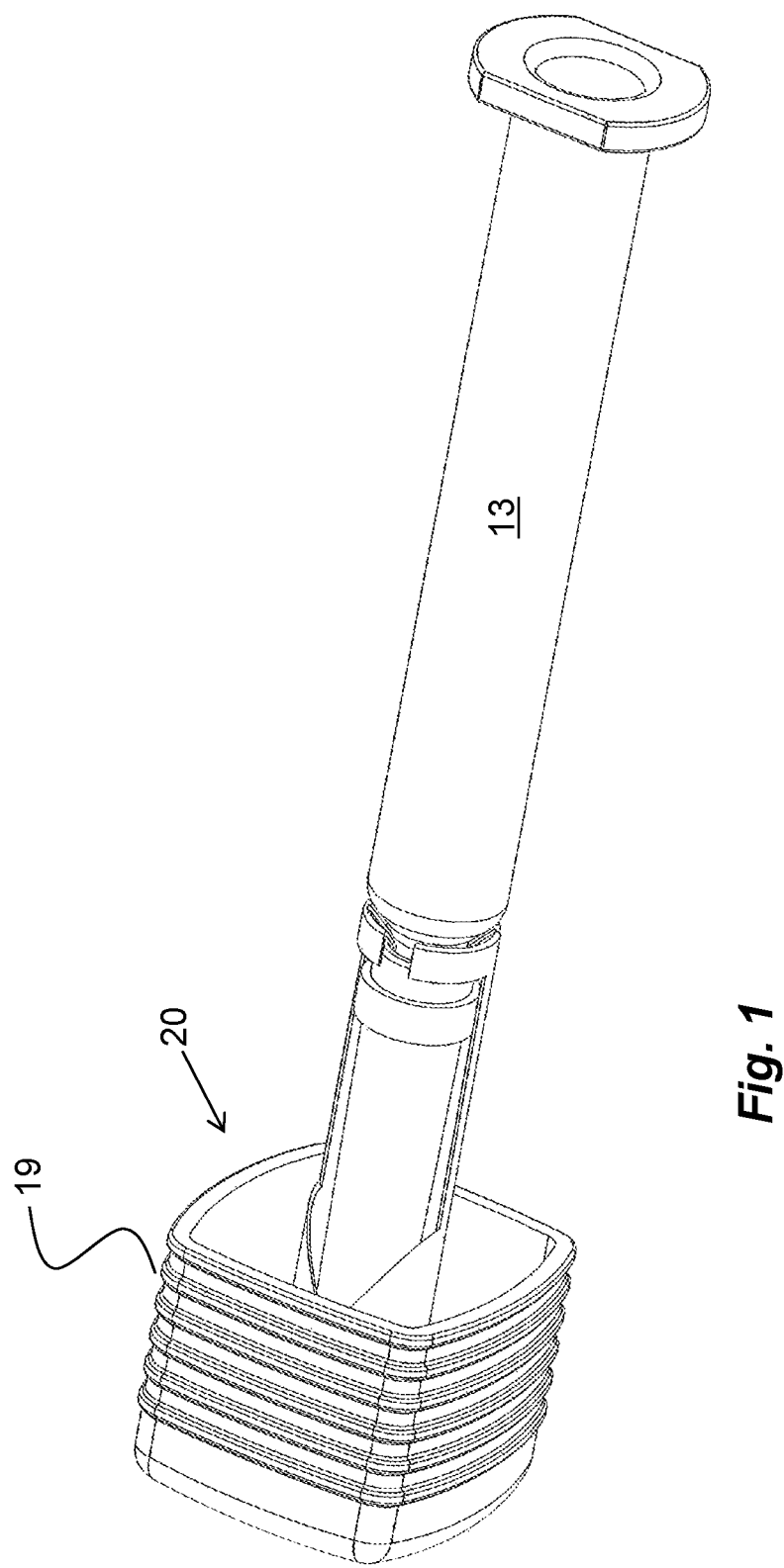
FIG. 1 is a perspective view of a medicament container provided with a needle shield remover of a protective cap.
Figure 2:
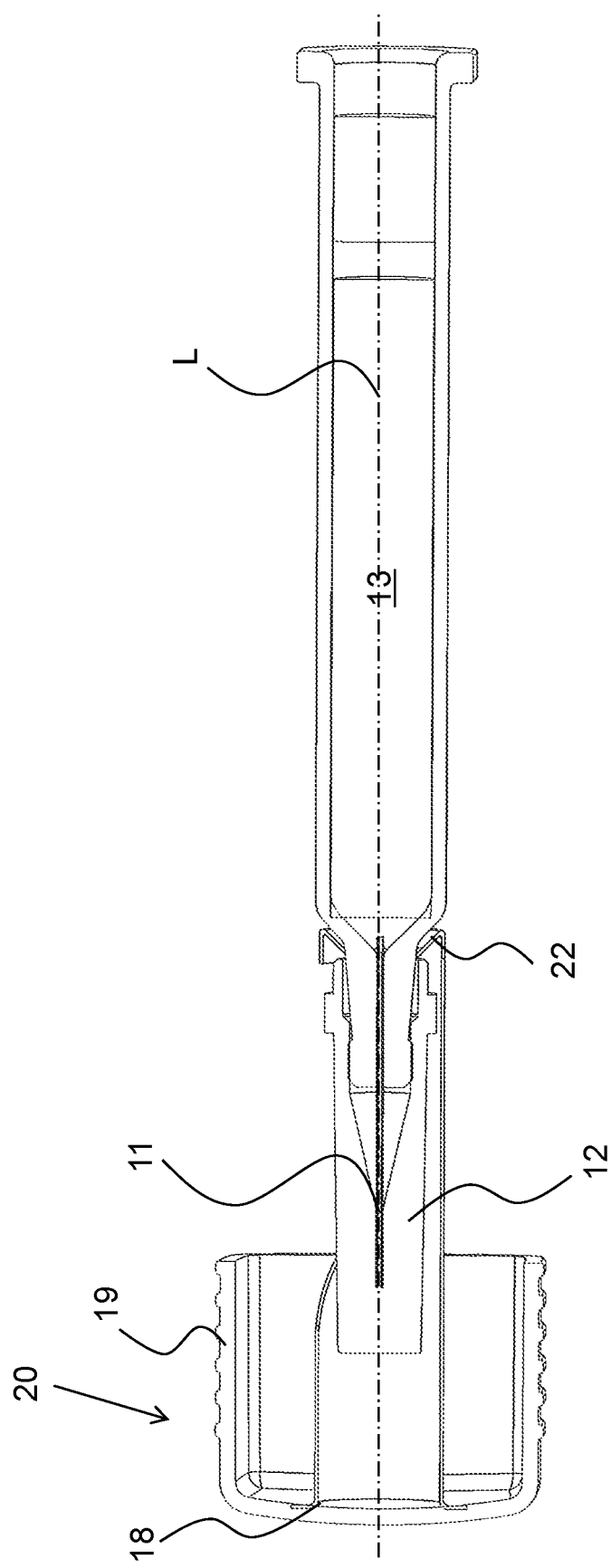
FIG. 2 is a cross-sectional view of the assembly of FIG. 1.

The disclosure pertains to a needle shield remover 10 that is to be used with for example a medicament delivery device. Before use of the medicament delivery device, an injection needle 11 of a medicament container 13, FIGS. 1 and 2, is protected by a needle shield 12, and often by a so called flexible needle shield, or FNS or a rigid shield remover, or RNS. The FNS is in this regard made of a soft, resilient material such as rubber and the RNS is provided with an outer shell or casing of a rigid material. In order to perform an injection, the needle shield has to be removed. In that regard, the medicament delivery device is arranged with a needle shield remover 10, FIG. 2.

Figure 3:
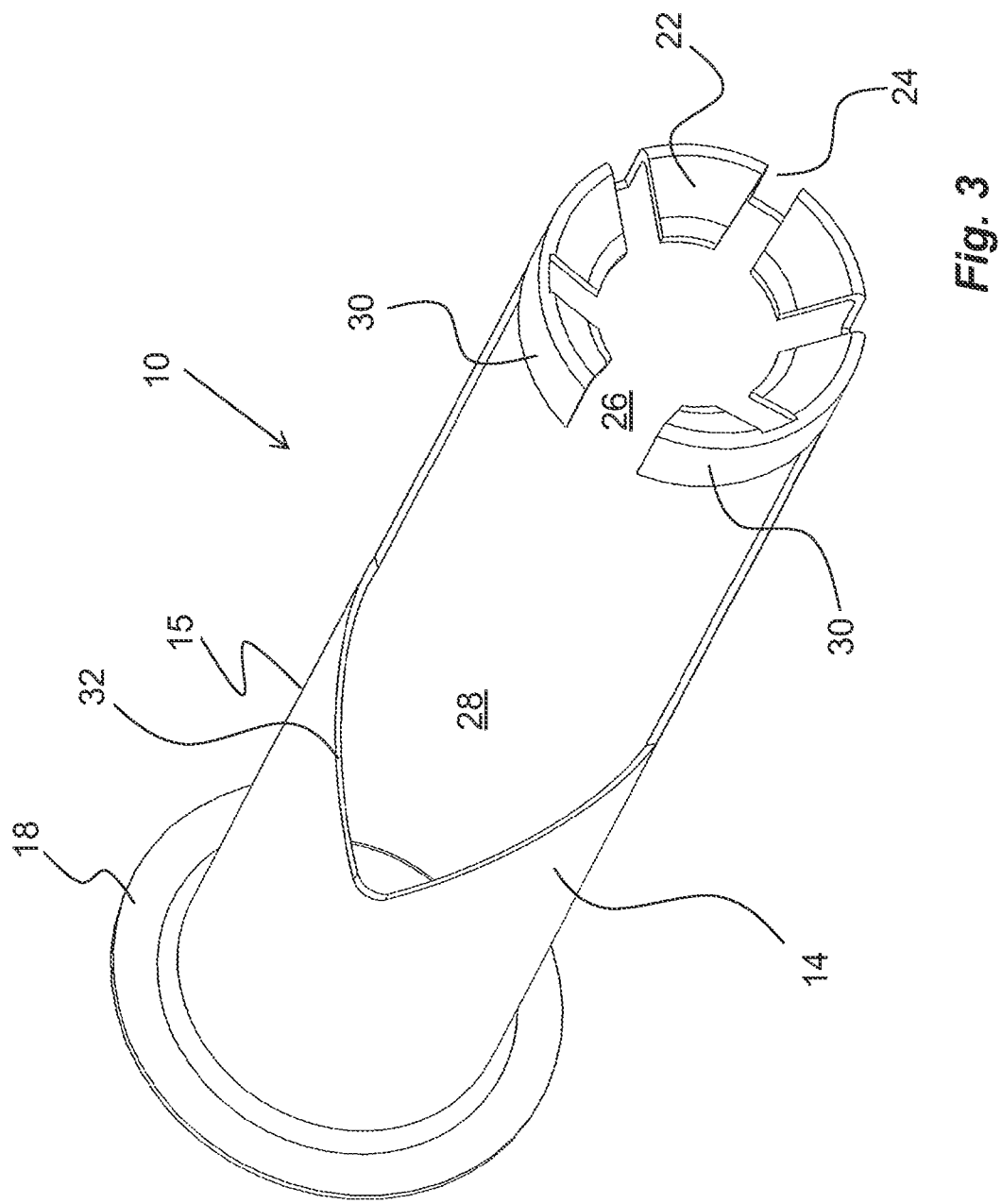
FIG. 3 is a perspective view of a needle shield remover according to a preferred embodiment.

In the embodiment shown in the figures, the needle shield remover 10 comprises a generally tubular elongated body 14, FIG. 3, having a longitudinal extension 15 extending in a longitudinal direction L. At a proximal end of the body 14, attachment elements 18 are arranged, such as a connector configured to engage a protective cap 20, that in the embodiment shown comprise an outwardly extending circumferential flange 18. The flange 18 as a connector is designed to fit with a grip part 19, FIGS. 1 and 2, of a protective cap 20 of a medicament delivery device (not shown) that is designed so that a user can grip and pull off the needle shield 12.

The needle shield remover 10 of the embodiment further comprises grip elements 22, FIG. 3, that are to interact with the needle shield. The grip elements comprise a number of radially inwardly directed tongues 22 at a distal area of the needle shield remover body 14. Moreover, the tongues 22 have an inclination in the proximal direction in relation to the longitudinal direction L. Moreover, first cut-outs 24 are provided between a plurality of the tongues 22, FIG. 3. One cut-out 26, a second cut-out, is in the embodiment designed somewhat wider than the rest. This second cut-out 26 is interlinked with a large third cut-out 28 that extends in the distal direction about halfway along the length of the body. The third cut-out 28 has a width so that generally half of the body 14 is removed as seen along the circumference. By this design, two band-shaped portions or sections 30 are formed on each side of the second cut-out 26. The third cut-out 28 terminates with a pointed shape of the distally directed end surfaces 32.

When a needle shield remover according to the described embodiment is to be attached to a needle shield, it is pushed with the distal end against a proximal end surface of the needle shield 12. This will cause the inclined tongues 22 to engage with the proximal end of the needle shield 12 and the band-shaped portions 30 will bias outwardly in the radial direction. The tongues 22 may also be biased due to their flexing properties in the radial direction. This will allow the tongues 22 to contact and slide along the side surface of the needle shield 12. The attachment is completed when the tongues 22 pass the distal end of the needle shield 12, FIGS. 1 and 2, whereby the band-shaped portions 30 and the tongues 22 can flex back to their initial position wherein the tongues 22 will be positioned behind the needle shield 12. Further movement of the needle shield remover is prevented because the distal end of the needle shield remover body 14 comes in contact with a shoulder portion of the medicament container 13 as seen in FIG. 2.

When the medicament delivery device is to be used, a user grabs the grip part 19 of the protective cap 20 to which the needle shield remover is attached via the flange. The protective cap 20 with the needle shield remover 10 is now pulled in the proximal direction. Due to that the tongues 22 of the needle shield remover body 14 are behind the needle shield 12, they will bring the needle shield 12 along as the protective cap 20 is pulled off. The injection needle 11 is now exposed and ready for penetration at a dose delivery site. Depending on the desired properties of the needle shield remover, it may be made of plastic material or of metal.

It is to be understood that the embodiment described above and shown in the drawings is to be regarded only as a non-limiting example of the disclosure and that it may be modified in many ways within the scope of the patent claims.

The invention claimed is:

1. A needle shield remover for a medicament delivery device, the needle shield remover comprising:
   a generally tubular body having a longitudinal extension and a proximal end;
   a number of grip elements arranged at a distal area of the body, the grip elements extending radially inwards from a circumference of the body;
   at least one longitudinally extending cut-out at said distal area of said body adjacent and between the grip elements; and
   a large cut-out that extends in a distal direction about halfway along the longitudinal extension of the body,
   wherein the grip elements are adapted to engage an outer surface of a needle shield when the needle shield remover is pushed onto the needle shield,
   wherein the at least one longitudinally extending cut-out adjacent the grip elements enables a generally radial outwardly bias of the grip elements during a pushing action that facilitates mounting of the needle shield remover on the needle shield, and wherein the proximal end is arranged with a connector for engagement with a grip part of a protective cap of the medicament delivery device.

2. The needle shield remover according to claim 1, wherein the longitudinal extension of the body extends in a longitudinal direction in relation to a length of said needle shield such that when the needle shield remover is mounted on the needle shield, said grip elements will extend past a distal end wall of the needle shield.

3. The needle shield remover according to claim 1, wherein the grip elements comprise a plurality of tongues.

4. The needle shield remover according to claim 3, wherein each tongue of the plurality of tongues has an inclination in relation to a longitudinal direction in a proximal direction of the body.

5. The needle shield remover according to claim 3, wherein the at least one cut-out comprises a plurality of longitudinally extending cut-outs that are arranged between adjacent tongues of the plurality of tongues.

6. The needle shield remover according to claim 1, further comprising a second cut-out adjacent the grip elements having a larger width than the at least one cut-out.

7. The needle shield remover according to claim 1, wherein a second cut-out adjacent the grip elements is interlinked with the large cut-out creating a band-shaped section at the distal area of the body.

8. The needle shield remover according to claim 7, wherein the band-shaped section has a larger width that constitutes generally half of the circumference of the body.

9. The needle shield remover according to claim 7, wherein the band-shaped section comprises two band-shaped portions formed on each side of the second cut-out.

10. The needle shield remover according to claim 7, wherein a proximal area of the band-shaped section is arranged with inclined surfaces.

11. The needle shield remover according to claim 1, wherein the connector comprises an outwardly extending circumferential flange.

12. The needle shield remover according to claim 11, wherein the flange is designed to fit with the grip part of the protective cap.

13. A protective cap for a medicament delivery device, wherein the cap comprises:
   an inside surface; and
   the needle shield remover according to claim 1 arranged on the inside surface.

14. The protective cap according to claim 13, wherein the cap is provided with a grip part.

15. The protective cap according to claim 14, wherein the protective cap is designed so that a user gripping the grip part will move the protective cap and the needle shield remover so that the needle shield will be pulled off of the medicament delivery device .

16. A medicament delivery device comprising:
   a medicament container with a needle;
   a needle shield attached to and surrounding the needle; and
   a needle shield remover according to claim 1.

17. The medicament delivery device according to claim 16 further comprising a protective cap, where the needle shield remover is attached to the protective cap through the connector.

18. The medicament delivery device according to claim 16, wherein the medicament delivery device is an injector.

\* \* \* \* \*